United States Patent [19]
Pomeroy et al.

[11] Patent Number: 5,559,032
[45] Date of Patent: Sep. 24, 1996

[54] METHOD AND APPARATUS FOR POST-TRANSFER ASSAYING OF MATERIAL ON SOLID SUPPORT

[76] Inventors: Patrick C. Pomeroy, 1920 Gilly La., Concord, Calif. 94518; Randall Madsen, 8970 Taurus Pl., San Diego, Calif. 92126; Wai P. Chan, 18845 California St., Castro Valley, Calif. 94546; Gary Lemke, 1630 St. David Dr., Danville, Calif. 94526

[21] Appl. No.: 386,202

[22] Filed: Feb. 9, 1995

Related U.S. Application Data

[63] Continuation-in-part of Ser. No. 206,249, Mar. 4, 1994, abandoned, which is a continuation of Ser. No. 862,023, Apr. 2, 1992, abandoned, which is a continuation-in-part of Ser. No. 547,167, Jun. 29, 1990, abandoned.

[51] Int. Cl.$^6$ ..................................................... C12M 1/36
[52] U.S. Cl. ................. 435/289.1; 435/307.1; 422/100; 422/116
[58] Field of Search ................. 435/289, 291, 435/299, 310, 311, 316, 808; 422/63–65, 67, 81, 100, 101, 114–116; 436/43, 46, 55, 174, 177, 180; 73/863.31, 863.32; 935/85–88; 222/92, 94, 25, 105, 394, 399; 141/114; 118/50, 425, 500

[56] References Cited

U.S. PATENT DOCUMENTS

| | | | |
|---|---|---|---|
| 3,756,459 | 9/1973 | Bannister et al. | 422/81 |
| 3,836,335 | 9/1974 | Eppes | 422/100 |
| 3,837,795 | 9/1974 | Becker et al. | 436/46 |
| 3,892,197 | 7/1975 | Kinney et al. | 118/429 |
| 4,087,327 | 5/1978 | Feder et al. | 435/287 |
| 4,147,278 | 4/1979 | Uhlig | 222/94 |
| 4,366,241 | 12/1982 | Tom et al. | 435/7.92 |
| 4,427,415 | 1/1984 | Cleveland | 436/177 |
| 4,477,578 | 10/1984 | Miles et al. | 422/100 |
| 4,522,923 | 6/1985 | Deutsch et al. | 435/7.92 |
| 4,598,049 | 7/1986 | Zelinka et al. | 422/116 |
| 4,618,586 | 10/1986 | Walker | 435/289 |
| 4,629,686 | 12/1986 | Gruenberg | 435/289 |
| 4,632,901 | 12/1986 | Valkirs et al. | 435/287 |
| 4,704,256 | 11/1987 | Hood et al. | 422/116 |
| 4,786,597 | 11/1988 | Matson et al. | 435/287 |
| 4,818,677 | 4/1989 | Hay-Kaufman et al. | 435/805 |
| 4,818,701 | 4/1989 | Littlehales | 435/311 |
| 4,822,742 | 4/1989 | Challberg et al. | 435/310 |
| 4,834,946 | 5/1989 | Levin | 422/101 |
| 4,839,297 | 6/1989 | Freitag et al. | 435/17 |
| 4,847,208 | 7/1989 | Bogen | 436/174 |
| 4,920,056 | 4/1990 | Dasgupta | 436/43 |
| 4,946,651 | 8/1990 | Liston et al. | 422/102 |
| 4,968,624 | 11/1990 | Bacehowski et al. | 435/287 |
| 4,978,507 | 12/1990 | Levin | 422/100 |

FOREIGN PATENT DOCUMENTS 2185166  8/1987  Japan ..................... 435/287

*Primary Examiner*—William H. Beisner
*Attorney, Agent, or Firm*—Schapp and Hatch

[57] ABSTRACT

A method and an apparatus useful as a secondary level assaying tool for qualitative and quantitative confirmation of results obtained by primary separation techniques and their correlation with a specific function or property of the tested sample. An apparatus is useful for the post-transfer development assaying on the solid support of the biological samples already assayed by standard separation techniques such as blotting or chromatography.

9 Claims, 9 Drawing Sheets

Microfiche Appendix Included
(1 Microfiche, 29 Pages)

| FIG. 9A |
| FIG. 9B |

METHOD AND APPARATUS FOR POST-TRANSFER ASSAYING OF MATERIAL ON SOLID SUPPORT

This is a continuation-in-part of U.S. patent application Ser. No. 08/206,249, filed Mar. 4, 1994, now abandoned, and entitled "METHOD AND APPARATUS FOR POST-TRANSFER ASSAYING OF MATERIAL ON SOLID SUPPORT"; which is a continuation of U.S. patent application Ser. No. 07/862,023, filed Apr. 2, 1992, now abandoned, and bearing the same title; which is a continuation-in-part application of the U.S. patent application Ser. No. 07/547,167 filed on Jun. 29, 1990, entitled "Development of Post Transferred Material on Solid Supports: Method and Apparatus", abandoned.

A listing of the computer programs used in this invention is appended as Appendix A—on one microfiche consisting of 29 frames.

BACKGROUND OF THE INVENTION

1. Field of Invention

This invention concerns a method and an apparatus useful as a secondary level assaying tool for qualitative and quantitative confirmation of results obtained by primary separation techniques and their correlation with a specific function or property of the tested sample. Particularly, this invention provides an apparatus and method for the post-transfer development on the solid support of the biological samples already assayed by standard separation techniques such as blotting or chromatography.

2. Background Art and Related Art Disclosures

The specificity and resolution of immunochemical, chromatographical, radiochemical, and other similar techniques led to their increasing application to problems in biochemistry, molecular biology, immunology, and genetic engineering. The ability to specifically determine and measure picogram quantities or isolate milligram quantities of various chemical and biological materials depends often on combination of several specific techniques which confirm and/or correlate results obtained with these techniques with some specific property inherent in the assayed material. Radiochemistry, ion exchange separation techniques, gel permeation chromatography, electrophoresis, affinity chromatography, immunochemical techniques including use of specific antigen-antibody binding and antibodies for specific high resolution assay of proteins, immunoprecipitation, protein purification, hybridization, and immunoblotting became techniques widely used for scientific, diagnostic and therapeutic applications. Often, however, even these highly specific techniques require that a secondary assay be performed for qualitative and/or quantitative confirmation of the results obtained by primary level assays. These confirmations are usually achieved by reaction with specific reagents to which the sample already processed on the primary level is submitted. Many of the primary level techniques are performed under conditions where it is either impossible or inconvenient to contact these already processed samples with the specific reagent needed for such confirmation. In such an event, after the primary separation, these samples need to be transferred into an environment where such confirmation techniques may be conveniently performed.

A number of assays have been developed that produce specific developmental processes applicable to various immunoassays. These assays are disclosed, for example, in U.S. Pat. Nos. 4,839,297, 4,818,677, 4,786,597, 4,632,901, 4,522,923, 4,427,415, and 4,366,241.

These patents generally describe a variety of apparatuses that utilize a reagent or chemical reaction chamber (housing) where said detection or developmental processes are performed. Typically, samples are placed into a reaction chamber in the vicinity of the biological sample where a biological transformation occurs which utilizes capillary action through which donor liquid or sample is applied as the determining force. The housing for absorbent material or for solid phase recipient matrix is used as a binding site for the immunoassay development where capillary reactions carry biological samples and position such samples for immunological detection and its analysis.

These capillary reactions, however, depend on the material of the sample, strength of capillary forces and on other criteria which may be and often are unpredictable and not uniformly useful for immunological detection in biological materials as well as in the gels, membranes, filters, etc. where such immunological reaction are usually assayed.

Moreover, for post-transfer development, it is often necessary to use several different reagents, which must be interspaced with washing and rinsing cycles to prevent undesirable interactions or contamination. These demands are not and indeed cannot be met by relying on capillary forces alone.

The idea of providing of ingress and egress of various solutions and reagents is not new. For example, U.S. Pat. No. 4,629,686 describes perfusion apparatus useful for maintenance of the organs and biological tissues by providing a dynamic system able to replenish exhausted nutrients from the culture medium by delivering a chemical substance in a controlled manner to a place where the organ or biological tissue are located. The apparatus includes a plurality of vessels containing a different known concentration of the same chemical substance. A computer controls and selects a flow and a concentration of the chemical substance in a step-like manner by simply switching from one vessel to another vessel in a controlled manner so that a concentration of the chemical substance is controllable at each and every point in time. The above apparatus is suitable for delivery of various concentrations of one substance or the mixture of substances to an organ holding chamber. It would not be suitable to deliver different reagents for post-transfer development of biological samples in predetermined sequences interspaced with one or more washing cycles.

Various apparatuses for immunohistochemical staining have been developed. For example, U.S. Pat. No. 4,847,208, discloses a device and method for automating immunohistochemical staining of biological material on glass slides. The device contains a chamber where the slide containing biological material is placed. The chamber is tightly sealed and the reagents are dropped through the opening in the overhead door and removed by aspiration. The method described is quite laborious and is not very convenient for performing multiple developments of samples in sequence.

The flexible containers capable of containing and maintaining fluid under sterile conditions are disclosed in U.S. Pat. No. 4,968,624.

The current invention provides a versatile apparatus and a method able to meet challenges and to accommodate multiple requirements for post-transfer development processing. Using this invention, such post-transfer development is efficient, rapid, without loss and waste of reagents and provides a maximal safety to the user.

SUMMARY

One aspect of this invention is a method and an apparatus for post-transfer assaying of material on solid support.

Another aspect of this invention is an apparatus which is flexible, convertible, and allows a multiple use and a combination of variable assays and reagents to afford a fast, specific, precise, and various post-transfer processing of biological samples or materials containing such samples.

Still another aspect of this invention is an apparatus comprising essentially the following components: a reaction chamber having a sample well; a reagent storage chamber having a means for holding pouches filled with various reagents, washing and rinsing solutions, fixating solution, staining material, and having further means for transporting these reagents and solutions in predetermined sequences, quantities and time periods to the sample well; a means for agitation of the sample well within the reaction chamber; a reagent reclamation system having reagent collectors; a vacuum providing means; a pressure providing means; and a means providing overall control over the criteria and conditions of the method for post-transfer development.

Another aspect of the current invention is an apparatus wherein the assay parameters and control over the sequences, timing, quantities, and choice of reagents are preprogrammed into a digital computer which is an inherent part of the apparatus.

Still another aspect of the current invention is a method for post-transfer development of biological materials, tissues, and other materials such as gels, membranes or filters containing processed biological materials.

Still another aspect of the current invention is a method wherein reagents or solutions stored in reagent holding pouches of the reagent storage chamber are transferred in amounts and sequences preprogrammed in the digital computer to a sample well containing a sample to be developed, and wherein said sample is submitted to a development or reaction with each particular reagent or solution one or more times for a time period which is preprogrammed in the digital computer and wherein the sample well is optionally agitated during the development or reaction, and wherein after each development or reaction the reagent is removed by vacuum and transported to a reclamation system collector, and wherein the developed sample is further submitted to post developmental determination of intensity, radioactivity, fluorescence, color, or other indicators of a quality or quantity of the biological sample or material.

Still another aspect of the current invention is the reclamation of the reagents or solutions for reuse by a modified reclamation system allowing a return of the reagents to their original pouches within a reagent storage chamber, by providing a vacuum in the reagent storage chamber to transport by suction the reagents from the reaction chamber back to their own pouches for reuse. In this aspect, the reagent storage chamber and the reaction chamber internal pressures are controlled by one pump which may alternatively provide either the pressure or the vacuum.

DETAILED DESCRIPTION OF THE INVENTION

Figure 1:
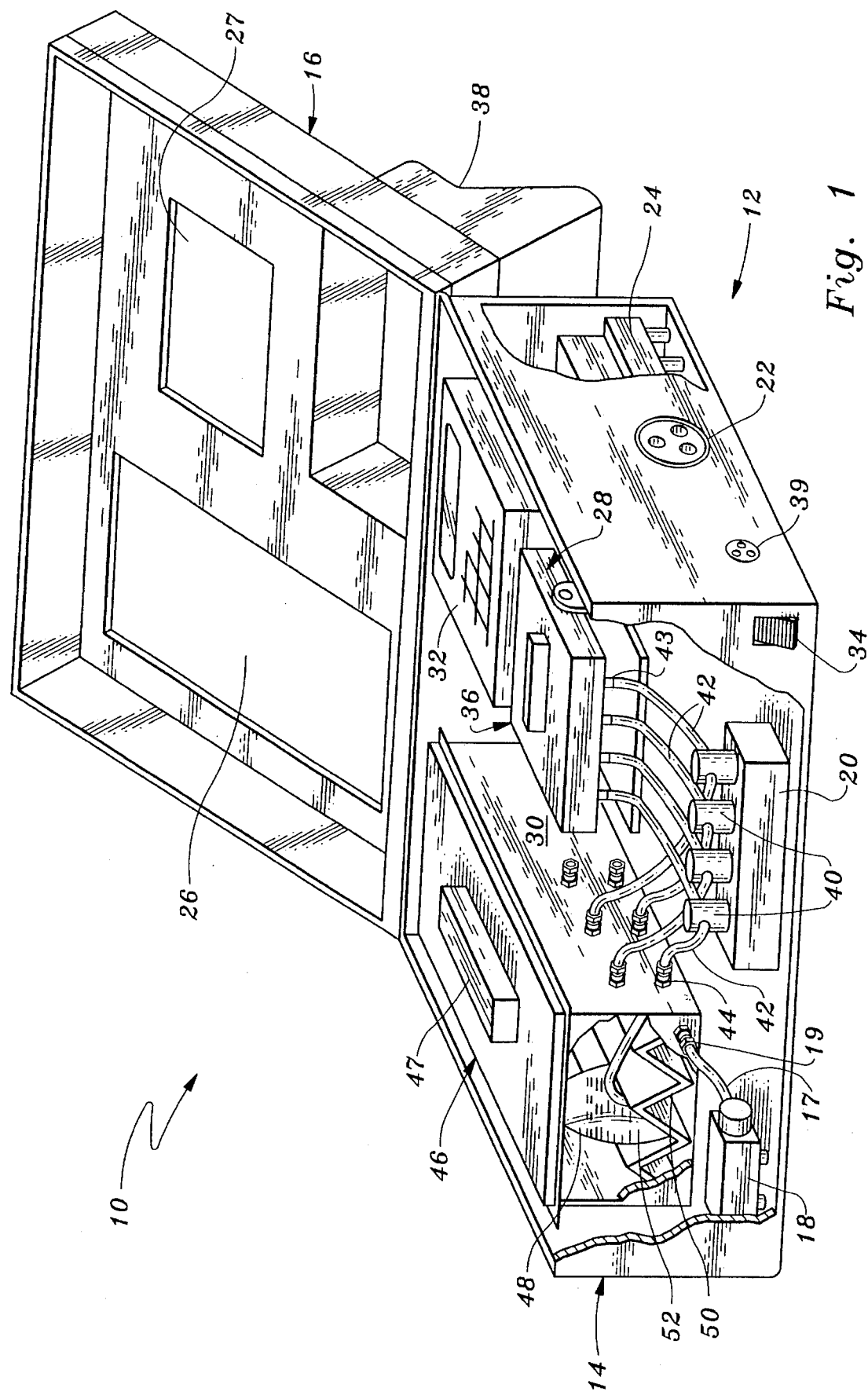
FIG. 1 is a three-dimensional view of the apparatus of the present invention, with its cover open, showing the critical components of the apparatus.

The apparatus and method of the current invention provide convenient, flexible, convertible, fast, specific, precise, and variable means to achieve, with maximum efficiency, post-transfer development on a solid support. The apparatus is easily programmable to perform and control single or multiple functions, to control timing, temperature, agitation, and reagent volumes for a number of consecutive protocols. Moreover, it easily accommodates variability of the experimental protocols and is convertible to allow these protocols to be quickly changed according to needs of the user.

The present invention thus provides a method and an apparatus which utilizes microchip computer technology to precisely control post-transfer developmental processes performed on membranes, gels or biological tissues which may contain protein or DNA within the structures of a solid support matrix. These processes are fully automated to allow fast, precise and reliable confirmation of DNA, DNA fragments, nucleic acid, antigen, antibody and antigen-antibody complexes identity and/or their quantitation.

The procedures for transferring proteins and nucleic acids are well developed, defined, precise, and standardized. Included in this group of well-defined processes are the protocols for the manipulation of gels and membranes after electrophoresis, transfer blotting immunoreaction, receptor bindings and formation of antigen-antibody complexes.

Using these well-defined procedures, the present invention utilizes a fully automated apparatus containing a functioning microchip computer to command activation and deactivation of flow control valves and air vacuum pumps within an apparatus of this invention, as described in detail below in FIGS. 1–9B. The microchip computer is preferably a PC type having a Microsoft DOS operating system, a compiler for C language, and a WordStar® word processing program resident in memory. Each valve and subsequent flow line dedicated to a specific chemical reagent directs the specific reagent into a reaction chamber wherein a membrane, gel filter or biological tissue is placed. A process to develop a membrane, gel filter or biological tissue begins with introducing a required sequence and protocol of reagents. Such sequences and protocols develop and detect a pattern, nature or specific quality or propensity of substances characterizing various biological materials and allows their identification and quantification.

An automated post-transfer system of this invention performs reproducible and reliable assays on membranes, gels filters or directly on biological samples. It accommodates stringent reagent usage requirements, washing efficiency, sample integrity, and protocol documentation. It is designed to perform a variety of accepted, programmable protocols based on user options. In addition, assays are performed utilizing sufficient amounts of valuable reagents, while keeping wastage at a minimum. Efficient reagent ingress and egress systems are used to supply, remove, reuse, and recycle valuable reagents. Thorough and efficient washing cycles needed between reagent applications in order to remove residues that could potentially result in misleading backgrounds staining are preformed automatically, allowing numerous washing and rinsing cycles. Specimen integrity is monitored and maintained at all times. A user-friendly software package is designed whereby researchers can easily program, document, and store various protocols. Finally, a large database of stored protocols can be made available to enable the instrument to be used as a multiuser piece if so desired.

The present automated system performs both immuno post-separation assays of gels and immuno post-transfer assays of membranes. It comprises a single housing, bench-top instrument containing a reaction chamber, a reagent storage area, a reagent delivery system, and a waste disposal or reagent recycling unit as described in FIGS. 1–8. The instrument is programmed and operates through an interface with user's IBM compatible PC system. A data acquisition digital input/output board such as a SCSI port or a standard serial port may be used.

The reaction chamber, molded of chemically inert polypropylene, was designed to have a sample well which accommodates multiple gels, membranes, filters or biological samples of a variety of sizes. It enables users to perform all washing, blocking, DNA probe introduction, antibody introduction, signal development, antigen-antibody complex formation, receptor binding, staining, and incubation procedures without manipulation of gels or membranes. The tight fitting coverplate prevents drying of the sample and undue loss of reagents by evaporation. The chamber is detachable for easy cleaning and for incubations at alternate sites. A larger reaction chamber is available to accommodate large industrial size samples. A further option is a built-in incubation processor interfaced with an accurate temperature regulating system and/or built-in reclamation unit for reuse of precious reagents.

The reagent storage area is designed to accommodate two or more, preferably six, separate reagent pouches, with the opportunity for expansion. Common reagents and washing solutions necessary for routine post-transfer protocols are prepackaged and available. Moreover, the pouches are designed to permit users to selectively load desired reagents for specific protocols. Each pouch can hold from 50 to 600 ml of solution and is supplied with positive release disconnects to prevent possible leakage of valuable reagents. These positive release disconnects allow users the alternative to store excess reagents, usually at 4° C., until further use is necessary.

The reagent delivery system to deliver and remove reagents and wash solution to and from the reaction chamber is based on positive pressure provided by a pump generating a sufficient pressure and/or vacuum, usually around 5 psi of pressure. Separate delivery lines connect each reagent pouch and wash solution to the reaction chamber. Each process line is separate and dedicated to prevent any possible cross-contamination. All delivery lines are kept to minimal lengths to reduce reagent loss in transit, and all junctions possess positive release disconnects to prevent leakage. Each delivery and removal line is controlled by a valve. All valve operations are computer-controlled and remain closed and fail-safe until directed to open by software command. This eliminates accidental operator errors. Optionally, the apparatus has a micro-delivery system that can supply as little as 0.25 ml of solution and recover down to a volume of 5 ml.

Waste solutions are channeled by separate removal lines to a central drain hose that can be accessed to laboratory disposal systems or are, preferably, channeled to reclamation pouches for subsequent reuse or are channeled back to their original storage pouches. These two last features tie in with the micro-delivery system for the recycling of precious reagents.

Now referring to individual figures, in particular to FIG. 1, the apparatus 10 comprises a housing and main frame 12 which has a hollow housing bottom 14. The housing bottom 14 is electrically grounded. In the preferred embodiment, the housing bottom 14 is rectangularly shaped. The main frame 12 has a cover 16, attached thereto in a conventional manner. The cover 16 fits tightly on the housing bottom 14 in order to prevent any exposure of electrical or mechanical components 18, 20, 32, and 24 which could cause an injury to the operator by accidental touching, or damage by spills, electrical shocks or otherwise. Preferably, both the housing bottom 14 and cover 16 are formed as one integral piece from thermoplastic materials, preferably from polypropylene or polyethylene.

Preferably, housing bottom 14 and cover 16 have the following dimensions: a height of about 30 centimeters; width of about 60 centimeters; and length of about 40 centimeters. However, the main frame 12 may have any shape and dimensions which would advantageously house all components necessary for its proper function. The above dimensions are given as a guidance, as they were shown to be convenient for apparatus' function.

The cover 16 has apertures 26 and 27 to allow an easy access to functional components of the apparatus, such as to a reaction chamber 28 and to a reagent storage system 30. Similarly, the housing bottom 14 has apertures 34 and 22 for various switches and electrical outlets.

Figure 2:
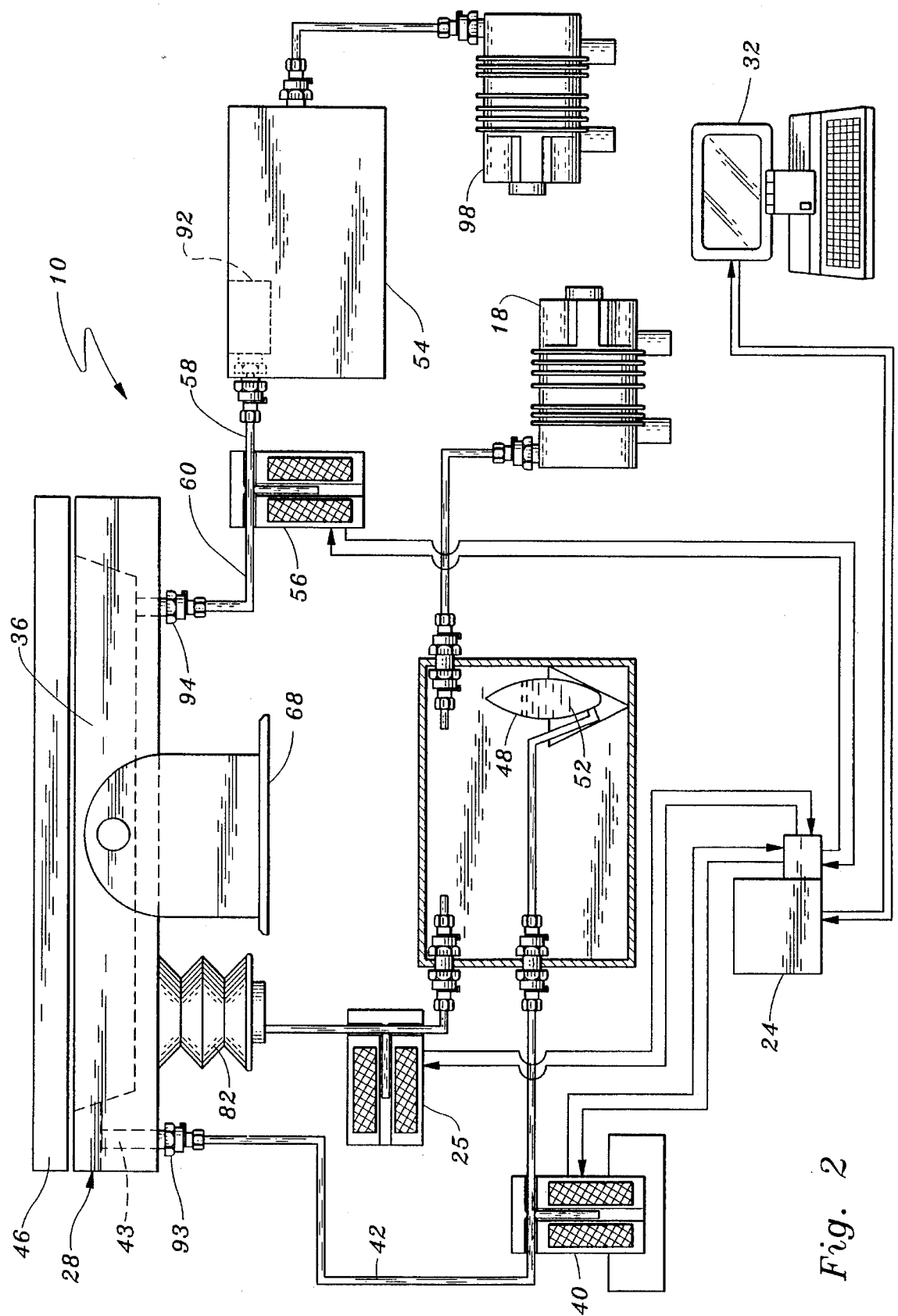
FIG. 2 is a diagram of the apparatus and the system of the present invention, with each component shown in its role and relationship to its specific function.

Optionally, the cover 16 is provided with a raised angular section 38 which permits the installation of a digital computer 32 attached thereto. Alternatively, the computer may be placed in close proximity of the apparatus 10 and connected therewith as seen in FIG. 2.

A housing for reaction chamber 28 is sunk into the housing bottom 14 and the connecting/disconnecting mechanism plugs 40 are interconnected with the reagent storage chamber 30 via connecting tubing 42 entering the reagent storage chamber 30 through apertures 44.

In accordance with a principal feature of the present invention, connecting tubing or tubular conduit 42 (FIG. 2) is provided at each end with a valved conduit coupling of the well known kind, which is capable of passing fluid only when connected to a corresponding, mating fixedly mounted coupler, of the well known kind, which is itself incapable of passing fluid unless it is fully interengaged with one of said valved conduit couplings.

A reagent storage chamber 30 has a lid 46 (FIG. 3) which allows opening the chamber 30 to refill the reagent holding pouches 48 with reagent 52. Each pouch 48 is connected with tubing 42 to the sample holding chamber 36 located inside of the reaction chamber 28 and the reagent 52 stored in the pouch 48 is supplied via tubing 42, when the use of the reagent is desirable. The pouches 48 are placed in the grid 50 (FIG. 6) to be minimally exposed to outside pressure and maximally protected against rupture or leaking. The tubing 42 is inserted through the pouch 48, having its end 49 submerged in the reagent 52 as seen in detail in FIG. 6.

In accordance with a principal feature of the present invention, each reagent pouch 48 is manually removable from reagent storage chamber or reagent pouch container 30 without tools.

Figure 6:
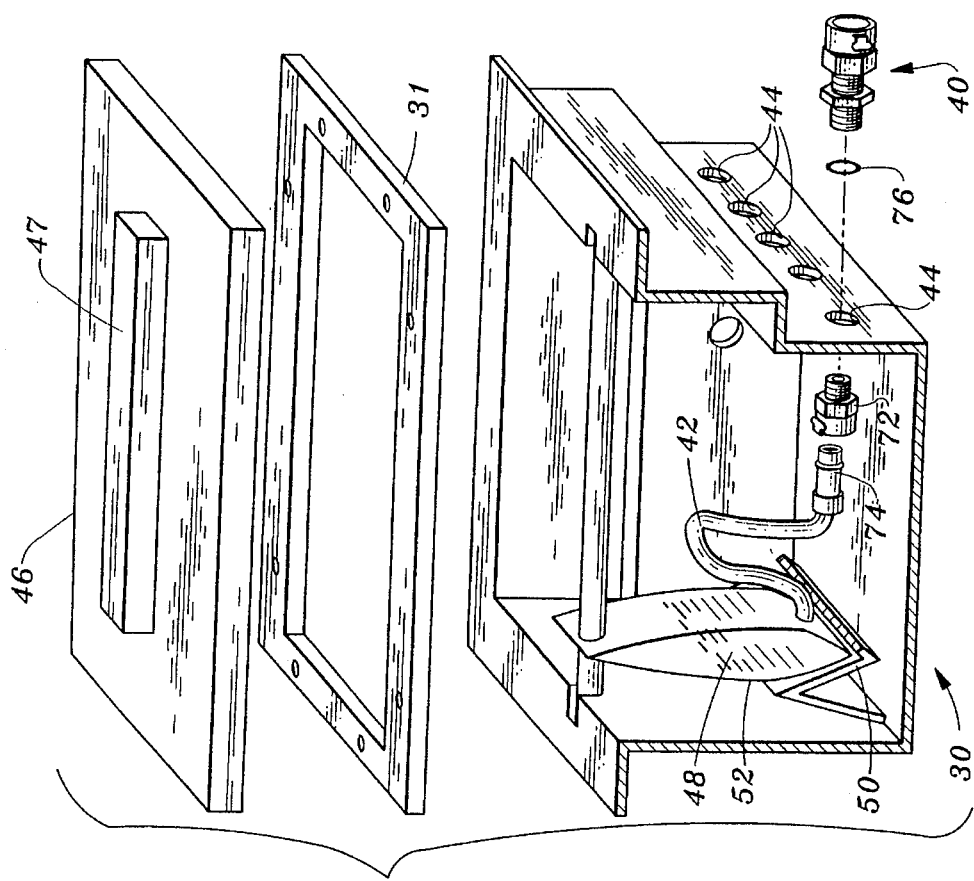
FIG. 6 is a representation of individual components of a dismantled reagent storage system assembly showing the relationship of various components.

In accordance with a principal feature of the present invention, as best seen in FIG. 6, each reagent pouch 48 is provided with a valved conduit coupling 42, 74 which is capable of passing fluid only when coupled to another valved conduit coupling, e.g., coupling 72.

A reagent storage chamber 30, in a preferred embodiment having a rectangular shape, contains numerous pouches 48 prefilled with reagents 52. The preferred embodiment of the reagent storage chamber 30 has a lid 46 which allows the chamber 30 to be completely sealed to allow the containment and pressurization of air within the reagent storage chamber 30. An air pump 18 is positioned beside or under the storage chamber 30 and is connected with the inside of the chamber 30 by connecting metal tubing 17 of which outlet 19 is positioned inside of the chamber 30. The air pump 18 pressurizes the chamber 30 with adequate positive pressure in pounds of air per square inch of sufficient force (psi) to squeeze the reagent pouch 48 to force the reagent 52 through the tubing 42 to enter the reaction chamber 28.

In accordance with a principal feature of the present invention, reagent storage chamber or reagent pouch container 30 is manually removable from housing bottom 14 without tools.

In accordance with a principal feature of the present invention, reactant-carrying body container or reaction chamber 28, is manually removable from housing bottom 14 without the use of tools.

The reaction chamber, having preferably a rectangular shape, functions as the site where a sample, such as a membrane, gel, or biological tissue is contained for post-transfer developmental testing process. Said reaction chamber is accessible through an aperture 27 in the apparatus housing 12. In the preferred embodiment, the reaction chamber protrudes above an aperture 27 in cover 16 so as to allow easy access to the said reaction chamber.

Reaction chamber 28 has a sample holding well 36 where the sample is physically placed before the testing. The sample holding well 36 may have different shape and size, both of which will depend on the shape and the size of the sample and may be exchangeable or permanently affixed to the bottom of well 36. The outlet 43 of the tubing 42 supplies the individual reagent 52 to the well.

The compact reaction chamber 28 provides protection from dehydration and contamination, eliminates the need for user manipulation, and is detachable for each cleaning and incubations. Reagents 52 are stored in sturdy, sterile, FDA-approved pouches 48 with positive release disconnects to prevent any possible leakage. Reagents are transported by positive pressure through a computer-controlled reagent delivery to the sample well 36 and a reagent recovery through separate lines 42 and 60, respectively.

In accordance with a principal feature of the present invention, short conduits, connecting tubings, or lines 42, 60, etc., are each provided at each end with one of said valved conduit couplings, each of which couplings is capable of passing fluid only when coupled to another, stationary, valved conduit coupling.

Such valved conduit couplings are well known in the prior art, and are generally commercially available. A typical one of such valved conduit couplings is shown in FIG. 6, and there identified by the reference numeral 74.

Fixedly mountable valved couplings capable of mating with and coacting with said valved conduit couplings are also well known in the prior art and generally commercially available. An example of such a well known fixedly mounted coupling is identified by the reference numeral 40 in FIG. 5.

As seen in FIG. 2, in operation, when the sample is placed into the well and the appropriate reagent for the post-transfer assay is chosen, the signal is provided either via computer or manually to a specific plug 40 which controls a connection between the well 36 and the reagent pouch 48. The plug opens and the reagent or the mixture of reagents from various pouches flows into the well 36 until the signal is deactivated and the plug 40 stops the flow of the reagent.

A pinch valve 20 which provides housing for plugs 40 acts as the control gate that responds to the digital computer 32 signals and allows flow of reagents from prefilled reagent pouches 48 to the sample holding well 36. In a preferred embodiment, the pinch valve assembly 20 comprises a series of valves to regulate the flow of reagents without undue loss of chemical reagent within transporting lines 42 attached thereto. Further, a preferred embodiment has the second pinch valve assembly 20 positioned between the reagent storage chamber 30 and the reaction chamber 28 and the well 36 so as to facilitate a short travel distance to allow rapid transfer of reagents.

A digital input/output board 24 is positioned within a housing 14 to facilitate the electronic switching control of a pinch valve assembly 20. In a preferred embodiment, digital input/output board 24 may comprise of solid state controls which are plugged into solder joints to complete interconnections between the pinch valve assembly 20 and the digital computer 32.

A digital computer 32 may be positioned within the main frame 12, or fastened to cover 16, or positioned outside of the apparatus 10 and connected to the apparatus 10, as described above.

FIG. 2 is a diagram incorporating schematically various components of the apparatus 10 with respect to their function within the post-transfer system. FIG. 2 indicates relationships and association of various components described in FIG. 1 and integrates components 18, 19, 20, 24, 32, 30, 36, 46, and 42 with a reagent reclamation system 54 described in detail in FIGS. 7 and 7A.

During the apparatus' performance, the digital computer 32 activates input/output board 24 and signals a pinch valve assembly 20 to open or close. Further, an air pump 18, when activated with alternating or direct current, supplies the reagent storage system 30 with sufficient air supply to exert external pressure upon a prefilled reagent pouch 48 to permit the transmittal activity thus transferring chemical reagent 52 from the prefilled reagent pouch 48 through the connecting tubing of the transporting line 42 to a reaction chamber 28 and to the sample holding well 36 which contains sample therein for the post-transfer developmental processing. A reagent 52 transported into a sample holding well 36 promotes the development of the sample, be it a membrane, a gel or a biological tissue. The reagent 52 is then retained in the well 36 for a time needed to develop the sample, or it just flows over the sample using a speed of the flow, as necessary for each assay and controlled by the computer.

In actual post-transfer development, one or more reagent, washing or rinsing cycles may be performed and combined as necessary for development of the color, separation, radioactivity, fluorescence or intensity of the sample membrane, gel, or biological tissue.

When the signal is received by the second pinch valve assembly 56 from the digital computer 32 and the pinch valve is activated by input/output board 24, the reagent 52 then is removed from the well 36. The reagent flows from the sample holding well 36 through transport line 58 to a reagent reclamation system 54, according to the principles of the invention disclosed further in FIGS. 2 and 7.

Figure 3:
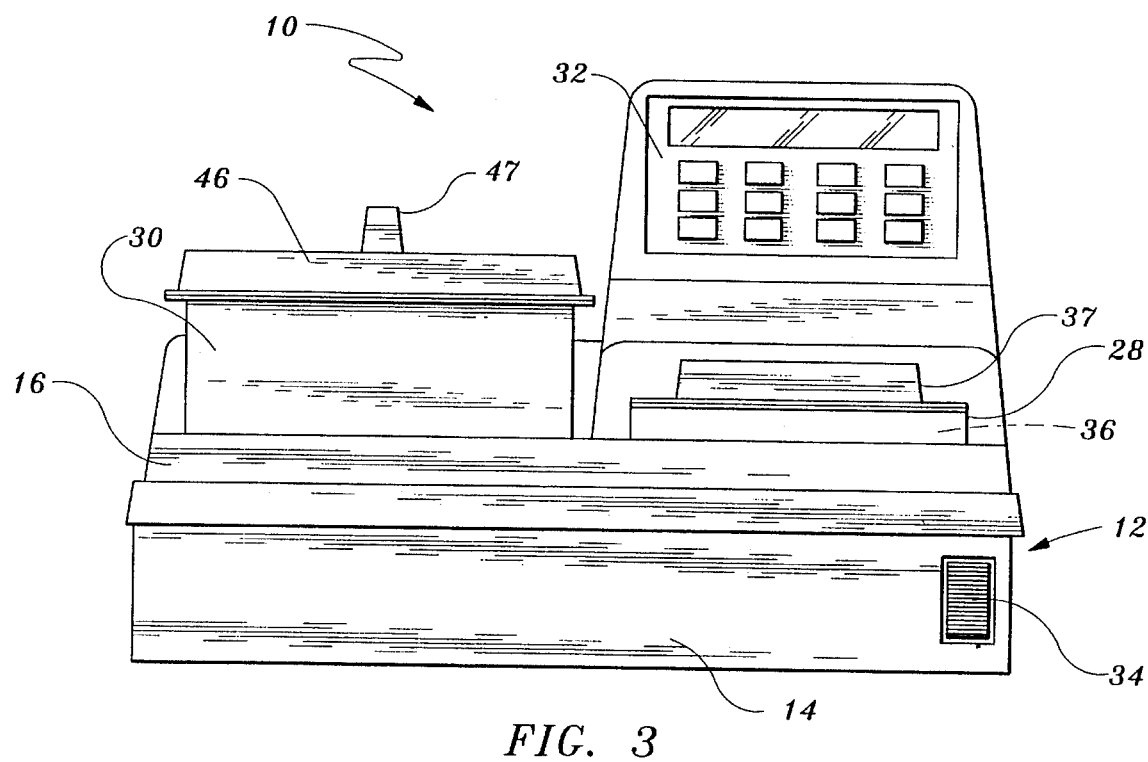
FIG. 3 is a front view of the apparatus of the present invention, showing an approximate location of a reagent storage system, a reaction chamber and a digital computer.

FIG. 3 is a side-view of the apparatus showing the position of the reagent storage chamber 30 covered with the lid 46 having a handle 47 for easy opening and closing of the chamber 30, and the position of the sample holding well 36 within the reaction chamber 28. In this particular embodiment, the digital computer 32 is positioned on the main frame 12 protruding through the closed cover 16. The upper parts of both the reagent storage chamber 30 and the reaction chamber 28 are also protruding through the closed cover in this particular configuration.

It is, however, contemplated that other embodiments and configurations of the apparatus 10 will be equally suitable for the purposes of this invention and they are intended to be within the scope of this invention. For example, one or both, the reaction chamber and/or reagent storage chamber may be completely sunk within the main frame of the apparatus 10 or there may be a flat platform, instead of the cover through which the reaction chamber and reagent storage chamber will protrude or be sunk into, in which case the cover 16 would be solid and when closed would cover all components completely to make the apparatus 10 portable.

In any case, as seen in FIG. 3, either configuration allows unobstructed access to the reaction chamber 28, digital computer 32, and reagent storage chamber 30.

Figure 4:
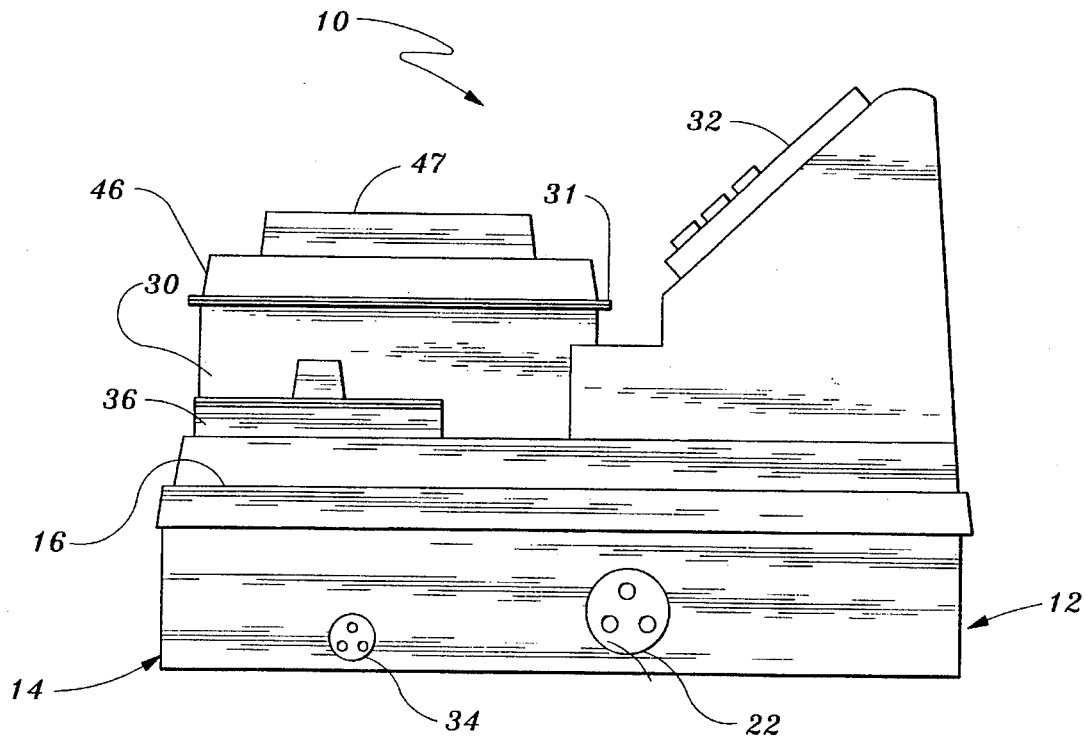
FIG. 4 is a side view of the apparatus of the present invention, showing approximate front to back location of a reagent storage system, a reaction chamber and a digital computer.

FIG. 4 is a side view of the apparatus 10, showing relative positions of the housing 12, cover 16, the reagent storage chamber 30, digital computer 32, and apertures 34 and 22 for receiving standard electrical connections. From this view, a seal 31 between the lid 46 and bottom of the reagent storage chamber 30 is visible. The seal 31 allows the pressurization of the reagent storage chamber 30, assuring that the pressure necessary for transfer of the reagents is maintained. The handle 47 allows an easy manipulation of the lid 46.

Figure 5:
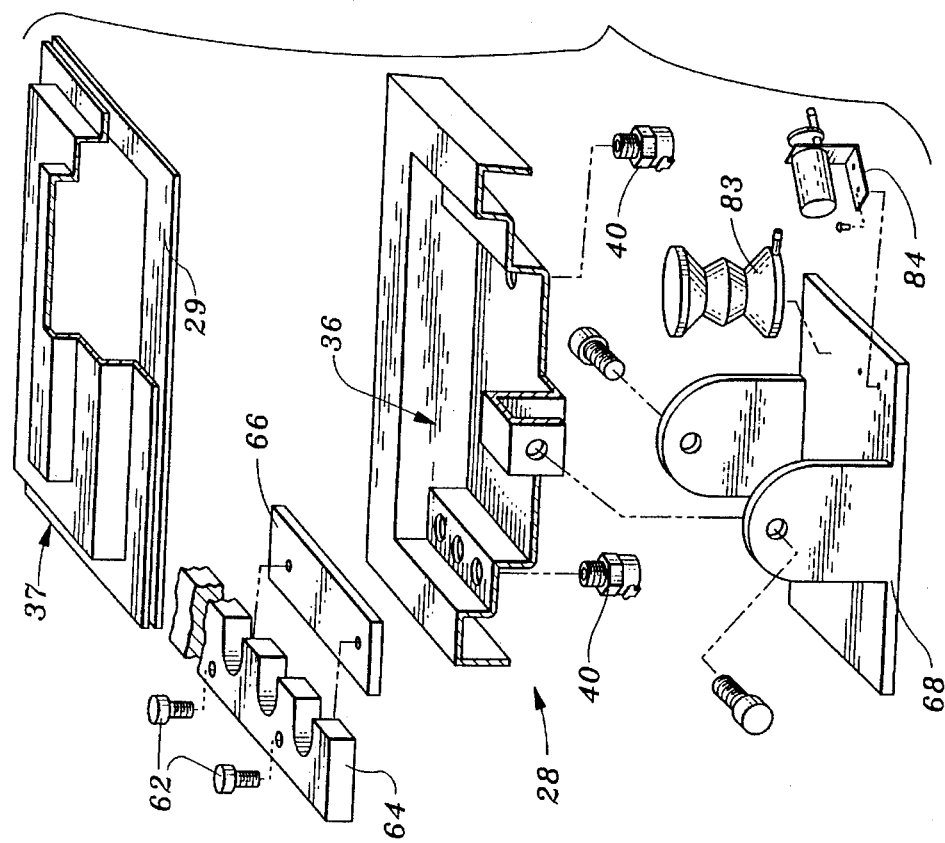
FIG. 5 is a representation of individual components of a dismantled reaction chamber assembly to show the relationship of various components.

FIG. 5 is an exploded view of a reaction chamber assembly and its position within the reaction chamber 28. The reaction chamber 28 contains a sample well 36 to accommodate a variety of samples in the form of membranes, gels or biological tissue. The reaction chamber 28 is preferably made of a thermoplastic material such as polypropylene. The reaction chamber 28 includes a series of apertures 27 into which fit plugs 40 which are represent connecting/disconnecting mechanism for tubes for delivery of reagents from reagent pouches. A seal 29 on the reaction chamber lid 37 creates an air tight fit when reaction chamber lid 37 is secured to said reaction chamber 28. Additionally, the reaction chamber assembly may contain a finger clamp 64 which, when secured by fasteners 62, will clamp and hold a gasketed valve 66, made of a stretched piece of silicon rubber, in such a manner as to create an uni-directional valve placed on the reaction chamber 28.

The reaction chamber 28 is positioned within the present housing 12 using a reaction chamber bracket 68. Further, the sample well 36 within the reaction chamber 28 may be agitated by means of an air bladder 82 and motor 84, attached as shown in FIG. 5. Bladder 82 moves to cause pivoting of the sample well about a mounting on bracket 68

In an alternative embodiment, the air bladder 82 can be made to agitate the reaction chamber by means of a pinch valve 25, which regulates air flow from the reagent storage system 30 to the air bladder. The air bladder inflates when pinch valve 25 allows pressure to enter it, causing it to elongate, as shown in FIG. 2.

FIG. 6 is an exploded view a reagent storage chamber 30 and its individual components. The reagent storage chamber 30 is provided with a series of 2–10 apertures 44 to accommodate the interconnection of the same number of plugs 40. One end of connecting tubing 42 is inserted through the wall of the reagent holding pouch 48 in such a manner that the pouch wall is impenetrably sealed around the tubing 42 and the end 49 of the tubing 42 is immersed in the reagent 52 and, connects the reagent chamber 30 with reaction chamber 28. The tubing is directed through the aperture 44, fastened to the lining 70 of reagent storage chamber 30 with fastener 74 and nut 72 on one side of the reagent storage chamber wall and with the plug 40 having a seal 76 on the other side of the reagent storage chamber wall. The prefilled reagent pouch 48 is positioned in such a manner as to facilitate accurate flow of a chemical reagent 52.

A seal 31 is placed between the chamber 30 and the lid 46 in such a way that it creates an air tight seal when compressed with a reaction chamber lid 46 and allows a build-up of the sufficient pressure to transport the reagent.

Figure 7:
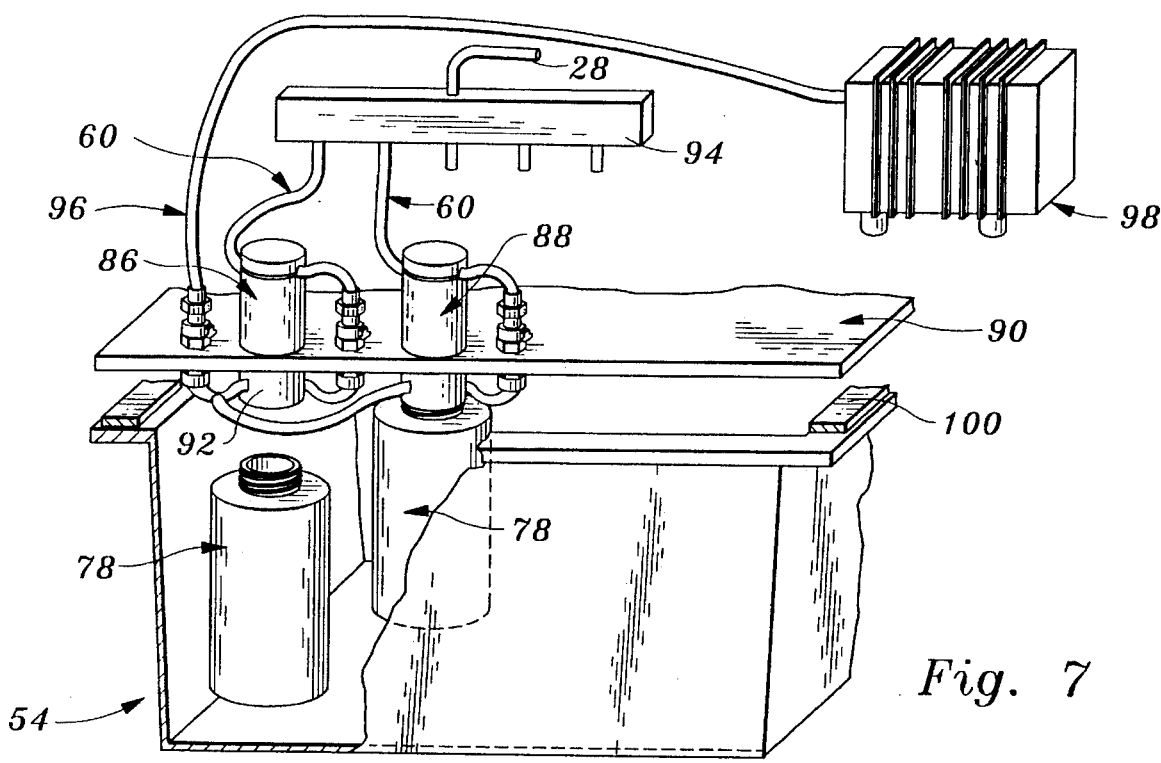
FIGS. 7 and 7B are a two dimensional representation of components comprising a reagent reclamation system.
Figure 7A:
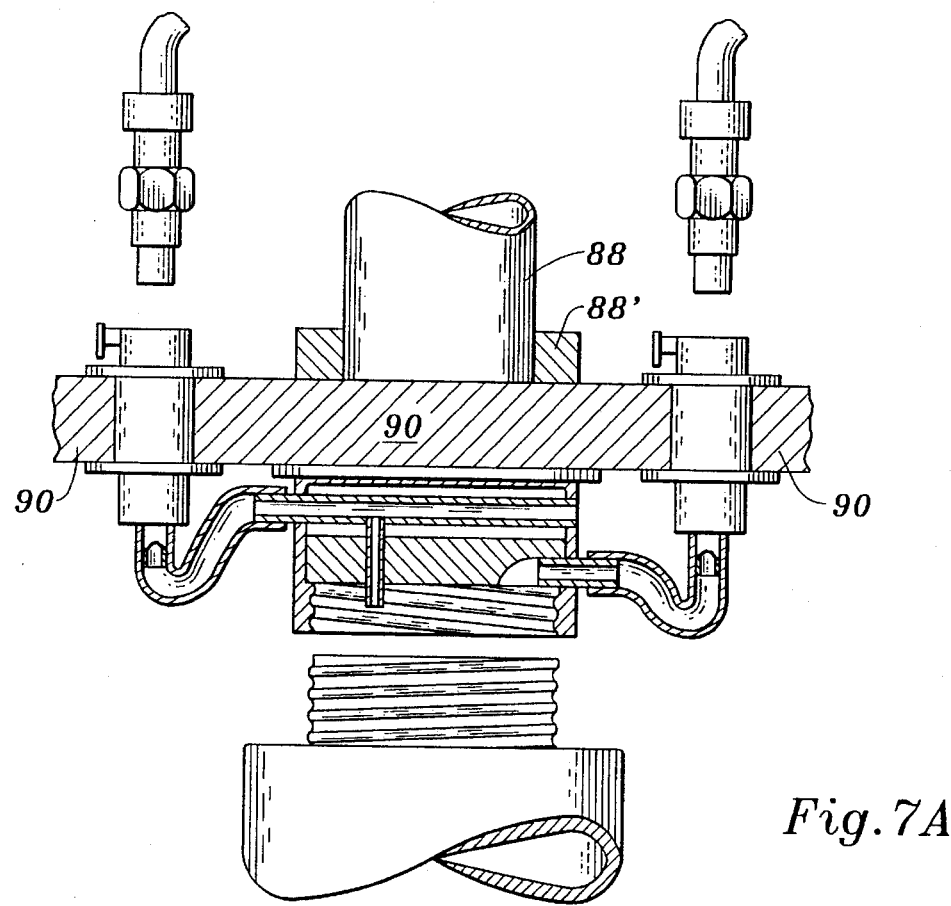

FIGS. 7 and 7A are a diagrammatic view of a reagent reclamation system 54. The reclamation system is constructed from a thermoplastic material, preferably from polyethylene. The operation of the reagent reclamation system 54 is controlled by a digital computer 32 via control of a series of valves, more particularly pinch valves 86 and 88 (88') positioned on a reagent reclamation lid 90. A reagent transport line 75 forming interconnection between a vacuum cap 92 and a waste manifold 94 transfers reagents from a reaction chamber 28 via tube 60 to a waste collector 78. The waste collector 78 is secured to a vacuum cap 92.

The vacuum cap 92 is connected with metal tubing 96 to a vacuum pump 98. The reagent reclamation system 54 collects various reagents 52 into selective waste collectors 78 that are connected to reaction chamber 30 through the manifold 94. The flow of reagents from the sample well 36 through manifold to the collector 78 is controlled by valves 86 or 88. The reagent reclamation system 54 has an essential vacuum gasket 100 sealing the reagent reclamation system under operating conditions.

The operation of the reagent reclamation system is interconnected with the operation of post-transfer assays. When the sample is placed in sample well 36 and the appropriate reagent 52 or the mixture thereof is selected and its transport from the reagent pouch 48 is effected, the reagent in effect either floods the chamber well and/or flushes or flows through the sample well 36 due to a pressurized inner space of the reagent storage chamber 30 on the side supplying the reagent to the sample well. Then, the reagent is moved through and out of the sample well 36 by the vacuum created by the vacuum pump 98. The vacuum pump is connected with a vacuum cap 92 which forces the reagent's collection into reagent waste collector 78. There are a number of waste collectors, exactly one for each reagent. In this way, each reagent is separated and there is a possibility of recycling or reuse. The hazards which of mixing various chemicals together are also avoided in this way.

In practice of the current invention, typically, the positive pressure exerted on the pouches containing reagents initiates delivery of various volumes of chemical reagents into the reaction chamber 28 containing a sample, such as a membrane, gel filter or biological tissue in the sample well 36. Through a computer digital program, a user chooses and creates a required atmosphere within the reaction chamber, and particularly in the sample well, and optionally allows agitation of the reaction chamber and the well containing the sample. The reagent volume is then removed by way of channeling reagent into a reclamation system 54 for waste disposal, recycling or reuse.

Typically, the membrane, gel, filter or biological tissue slide is placed into a sample well 36 of the reaction chamber 28. Then, the computer is called upon and pre-established programs of developmental protocols are chosen. The desired program specific to the nature of the sample or material is initiated. Choosing of the appropriate program activates the apparatus to begin the post-transfer development.

The reagent-filled pouches 48 which are connected to the process lines 42 leading directly to a reaction chamber 28 are computer activated by way of an air pressure generated from an internal air pump 18 located within the apparatus mainframe. The air pump 18 supplies an integrated reagent storage system 30 with adequate pressures to force the reagent 52 to flow through the connecting line 42 toward the reaction chamber 18. As a result, the chemical reagents are delivered to the reaction and the sample well.

The invention employs within the design of a reaction chamber and its sample well a number of independent entry ports 43, thereby maintaining integrity of chemical reagents and preventing cross contamination of separately delivered reagents. Such contamination could lead to poor development of membrane, gel, filter or biological tissue slide during developmental stages. After an introduction of a specific chemical reagent, a membrane, gel, filter or biological tissue is exposed to the reagent for certain time which vary according to different protocols. The time may vary from 1 minute to 360 minutes or even longer if necessary. The contents of the sample well 36 including the reagent or washing or rinsing solution may be agitated by air bladder 82, or heated, incubated, treated with slight pressure or vacuum or submitted to some other such environments with the other attached components. The reagent or solution is then removed and channeled to manifold 94 and subsequently either diverted into a reclamation chamber system 54 where the used chemical reagent is directed to its own waste collector 78 and held for reclamation or for proper disposal. This method is particularly useful for recovering, reuse and recycling of expensive reagents, such as DNA probes, which may be used again for additional probing on similar matrices.

Reagent-filled pouches can be easily removed from the reaction storage chamber for incubation, refill replacement, cleaning or long term storage at alternate sites.

The current invention, as briefly described above, is useful for developmental purposes and provides hands off operation with minimal labor requirements. No manual changing of potentially hazardous chemical reagents or physical manipulation of a possibly contaminated sample is required.

The apparatus is fully automated for simple or multiple transfer development. It is programmable to control timing, to control temperature, to control agitation, and to control the available reagent volume for single transfer. The apparatus and the method are suitable for automated multiple transfer development by providing multiple inserted reaction chamber, multiple single channel ports, multiple consecutive protocols which may be the same or different. It also allows automated reclamation of reagents by providing multiple collection sites, thus allowing hazardous waste control and preventing hazards and accidents due to high reactivity of some of the used reagent and contamination by samples elements.

The method of the current invention is particularly useful for identification or confirmation of, for example, antigen-antibody complexes, proteins, peptides, DNA and DNA fragments, nucleic acid and nucleic acid chains receptors bindings, etc. These confirmatory secondary developments are applicable, particularly, as complementary to an electrophoresis, preferably to gel electrophoresis and to immunoreactions on gels, filters or membranes.

Electrophoresis is a method whereby charged molecules in solution migrate in response to an electric field. The rate of migration or mobility through the field depends on the strength of the field and on the net charge, size, and shape of the molecules. The ionic strength, viscosity, and temperature of the medium also affect the way the molecules move. This process is used to study the properties of charged species and can also be used to separate these same molecules according to their charge and size.

In genetic research, medical research and forensic investigation, DNA's are frequently separated by electrophoresis on agarose gels and then immobilized onto a solid membrane support, such as a nylon or nitrocellulose membrane. Using restriction enzymes and other nucleic acid digestive enzymes, many DNA and RNA sequences can be fragmented to multiple pieces of various sizes, bearing different sizes and/or charges, which are then separated by electrophoresis. One can develop these electrophoretically separated bands for visualization by staining after they are immobilized onto a membrane support. In order to identify a specific sequence of DNA, synthetic oligonucleotide probes have been developed to hybridize against such fragments that are immobilized on the membrane.

Gel electrophoresis can be used to separate proteins, as well as DNA, into characteristic bands subsequently stained and visualized. One-dimensional gels were found to be quite satisfactory at first. However, as more complex systems demanding greater resolution appeared, new two-dimensional gel systems were developed. Today, hundreds of polypeptides or other molecules can be separated. Until recently, separation and visualization were thought to be adequate, but then the question surfaced as to the possibility of unequivocally correlating a specific band or spot obtained on an electrophoretogram to a specific function or a property which can further distinguish it. Pinpointing such a specific function by an antibody-antigen reaction from proteins separated by gel electrophoresis, for example, demand the formulation of complex post-separation techniques. The automation of these techniques is the subject matter of this invention.

In developing post-separation protocols, many parameters need to be considered. Since proteins are denatured prior to electrophoresis, questions arose as to how can proteins retain their antigenicity so that they will react specifically later.

Many of these difficulties have been overcome, and methods are now available to identify specific enzymes, antigens, or hormone receptors using immunostaining techniques, autoradiography, scintillation spectroscopy, and many other processes. These procedures, however, normally necessitate multiple manipulations including extensive incubations and repeated washes of fragile gels. They involve time-consuming operations, often prone to handling accidents, such as breakage and tearing of wet gels or cracking of drying gels. In addition, the identification of the resolved polypeptide bands generally requires relatively large amounts of reagents such antibodies which are usually available in short supply. Moreover, many of the primary separations use radioactive tracers or standards and their manual handling may be hazardous or impractical.

A major breakthrough in post-separation techniques came with the advent of protein blotting, that is, the transfer of protein band patterns from gel to solid support or membrane such as nitrocellulose or nylon. By transferring electrophoresis bands from a gel to a solid support, wet membranes became pliable, easy to handle and not prone to breakage; the immobilized proteins were accessible to ligands, transfer analysis required smaller amounts of reagents and processing times (washing and incubations) could be significantly reduced. Also, multiple replicas of a gel could be made, transferred patterns could be stored for months prior to use, the same transfer could be used for multiple successive analyses and the transferred protein patterns were more amenable to analyses that would be extremely difficult or impossible to perform on gels alone.

In general, protein blotting is the process of elution of polypeptides from a gel to an immobilizing matrix. Polypeptides can be eluted from the gel by three different techniques. The simplest technique is by diffusion whereby the gel is sandwiched between support screens. The whole unit is submerged for 36–48 hours in a large column using 2–3 l of buffer, and the proteins simply diffuse from gel to membrane. Clearly, the method is too long to be practical.

The second method of protein blotting is by capillary action. The gel is placed in a reservoir of buffer, a membrane is applied to it, and paper towels are layered above the membrane. The mass movement of buffer drawn up by the towels acts as the driving force to elute the proteins from the gel to the membrane. While this technique is more efficient and takes only 24–36 hours, it is still not practical for routine use.

The more widely used procedure of electroeluting polypeptides entails an electric current as the driving force. The gel and membrane are sandwiched much like the diffusion method, but they are inserted into a tank of transfer buffer, whereby an electric current is applied to drive the proteins onto the membrane. Though this method takes only 12–18 hours, it produces only one transfer at a time, and it needs large amounts of transfer buffers. Clearly, a less time-consuming technique capable of producing multiple blots with greatly reduced buffer requirements was needed.

These requirements were met with the advent of the semi-dry transfer technique and ultimately led to a development of this invention allowing the automation of the whole process. This process utilizes a semi-dry transfer blotter for the elution process. Eluting stacks composed of transfer units layered with filter paper (presoaked in the appropriate transfer buffers), gel, membrane, filter paper, and partition tubing (to separate one unit from another) can be stacked one on top of another. This final stack is placed in the semi-dry transfer blotter, and an electric current is applied for elution. With this method, as many as six blots can be performed simultaneously in only 10–30 minutes with greatly reduced buffer quantity requirements.

All of these innovations in the post-separation processes have eliminated the need to manipulate fragile gels, greatly increased the number of blots per transfer, and drastically reduced transfer times and buffer usage.

As the solid membranes still need to be qualitatively and quantitatively assayed, and as doing so by immunostaining or by multiple manipulations still involves multiple manipulations with extensive washings and incubations the advantage provided by the current invention is clear. The current invention, which concerns an automated post-transfer system, eliminates much of the labor-intensive and hands-on chores, allows processing of larger number of samples and afford safety features to prevent hazards and exposures to contaminated material.

Figures 8, 8A, 8B:
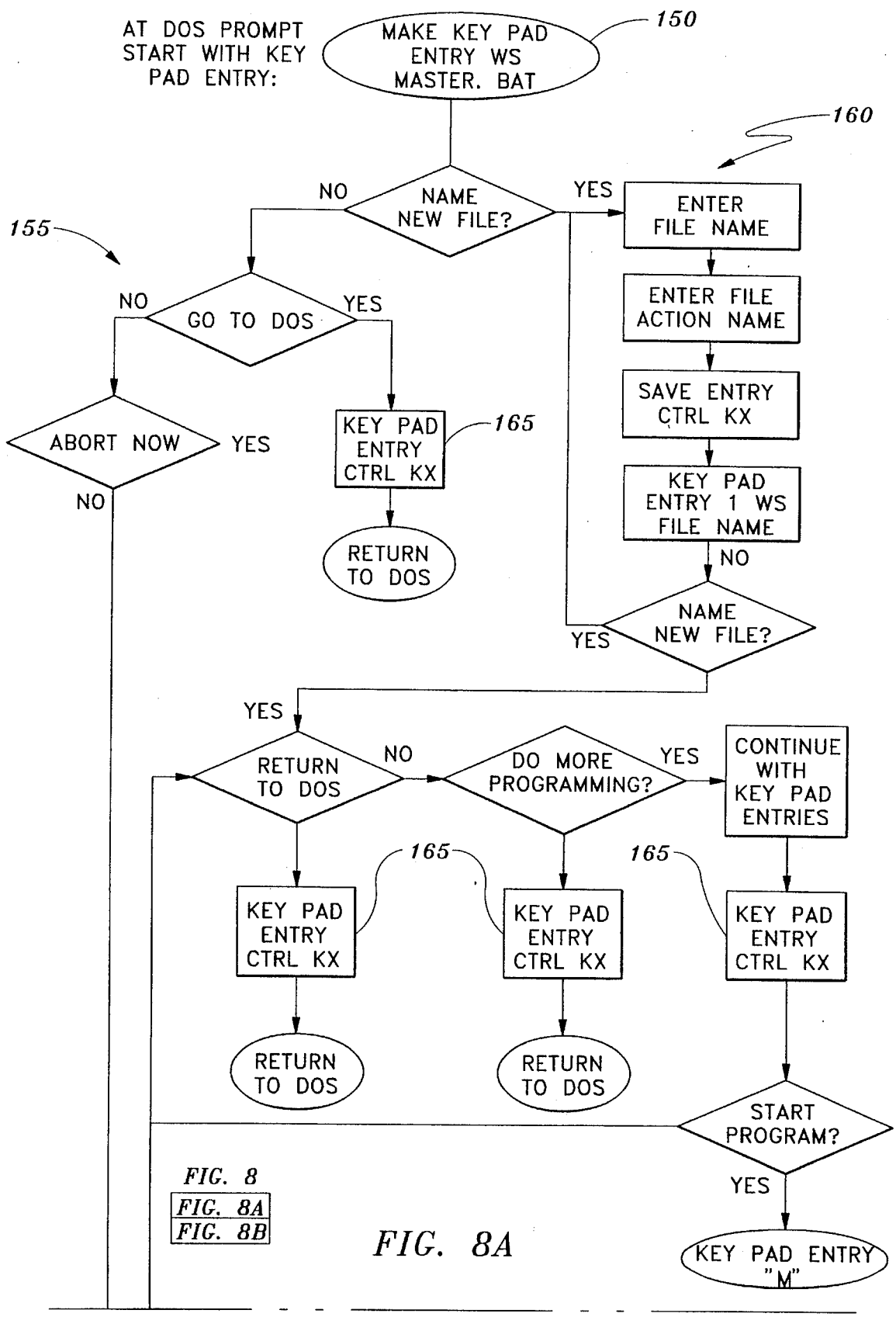
FIGS. 8A and 8B are a flow chart illustrating a preferred computer program for entering data and developing programs to control the present apparatus.
Figure 8B:
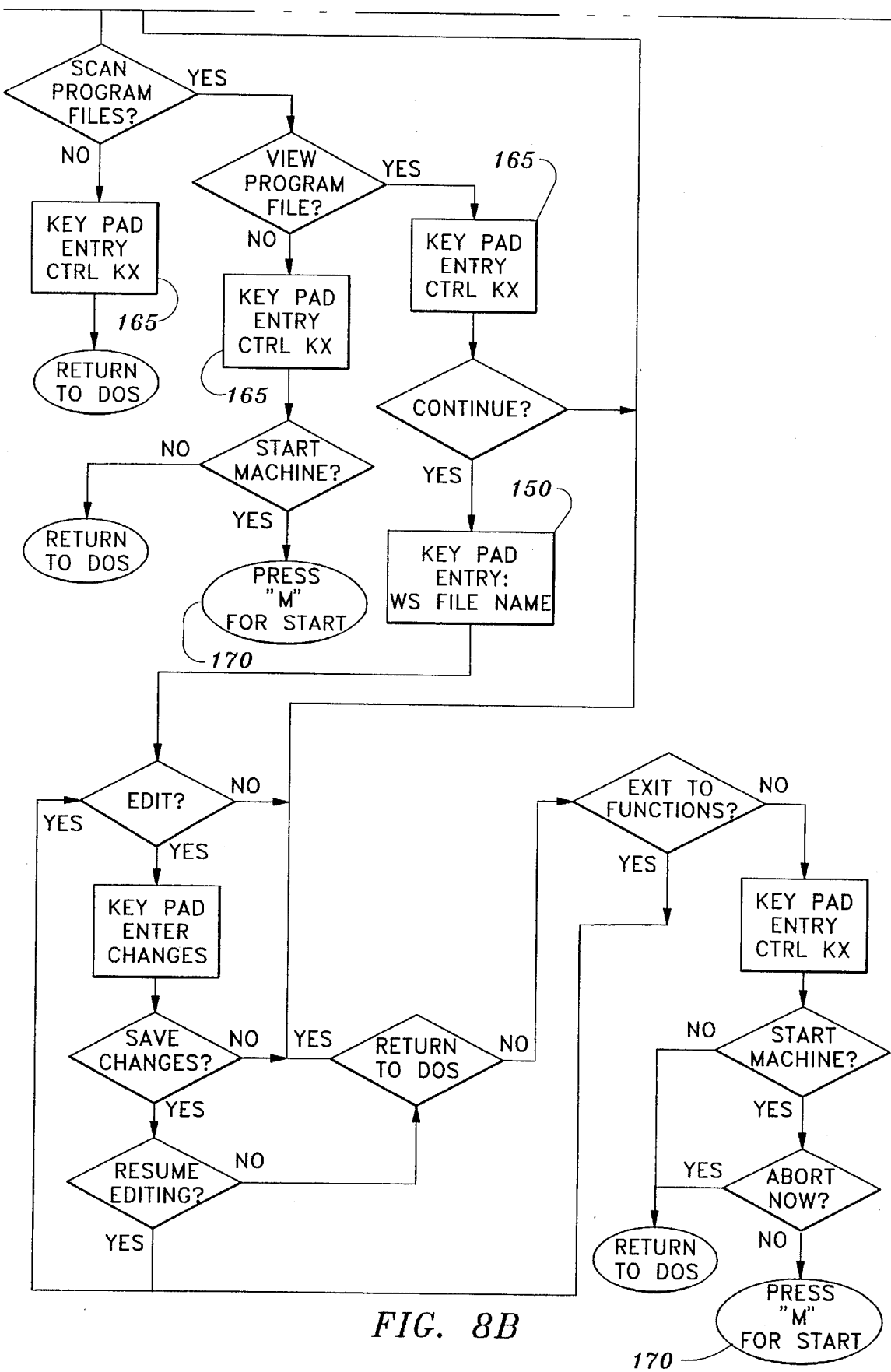

FIGS. 8A and 8B are a flow chart in conventional computer programming format, describing the operation of the program included herewith as Appendix A. The program essentially allows the retrieval, editing, or creation of a program file which controls the inflow, outflow and agitation/incubation of various reagents from reagent pouches 48 to the reaction chamber 28.

Following initialization of the present computer program, as seen in FIG. 8A, operation #150, the operator is presented with a number of options, such as creating or amending sequences or running samples. Control of the device by computer 32 is accomplished through a control program written in the higher level language C (a listing is appended in Microfiche). This C program acts as an interface for a word processing program, in this case WordStar®, available from WordStar International Incorporated, 201 Alameda del Prado, Novato, Calif. 94949. Thus, the initial command, the PC or the like is WS Master.dat (FIG. 8A, operation block 150). This initiates WordStar and calls up the master data base. The flow chart in FIGS. 8A and 8B illustrate how an existing file may be used (branch 155) or how a new file is created (branch 160). A task is achieved by simply calling out the main menu and specifying desired protocol sequences. The operator is led through a series of programming steps to achieve specific tasks. When choosing a specified method, specific reagents, incubation times, and wash cycles are entered through keyboard commands. Up to 100 sequential methods are stored and selected for future runs in order of program entry. Although the system is designed to run only one program process at a time, the operator has the power to dictate reagent injection to be applied at any time. The instrument is totally flexible and achieves efficiency with regard to throughput when samples are being processed using single methods with common reagents.

Figures 9, 9A:
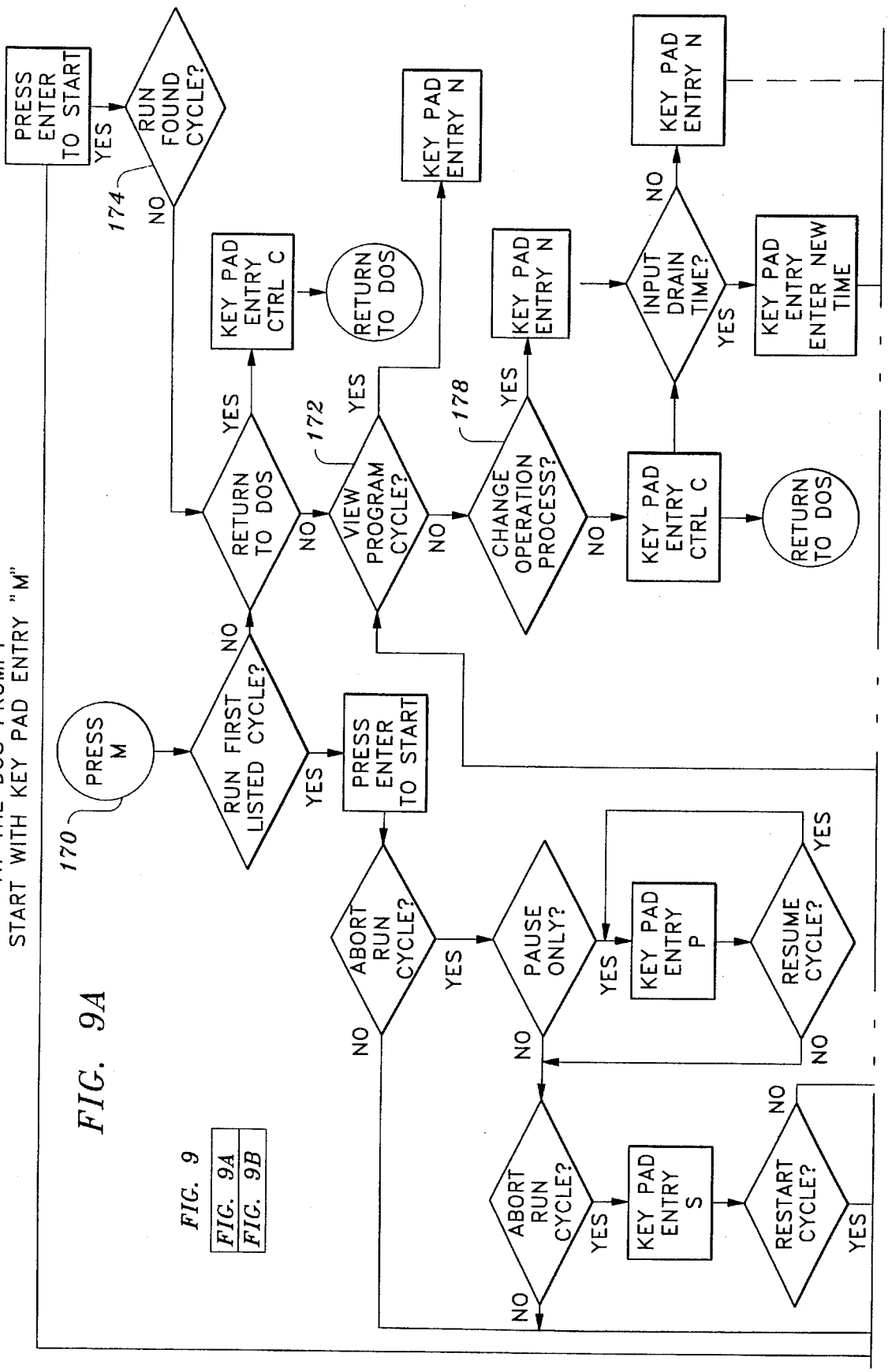
FIGS. 9A and 9B are a flow chart of the program that operates the present apparatus based on data and programs entered in the flow of FIGS. 8A and 8B.
Figure 9B:
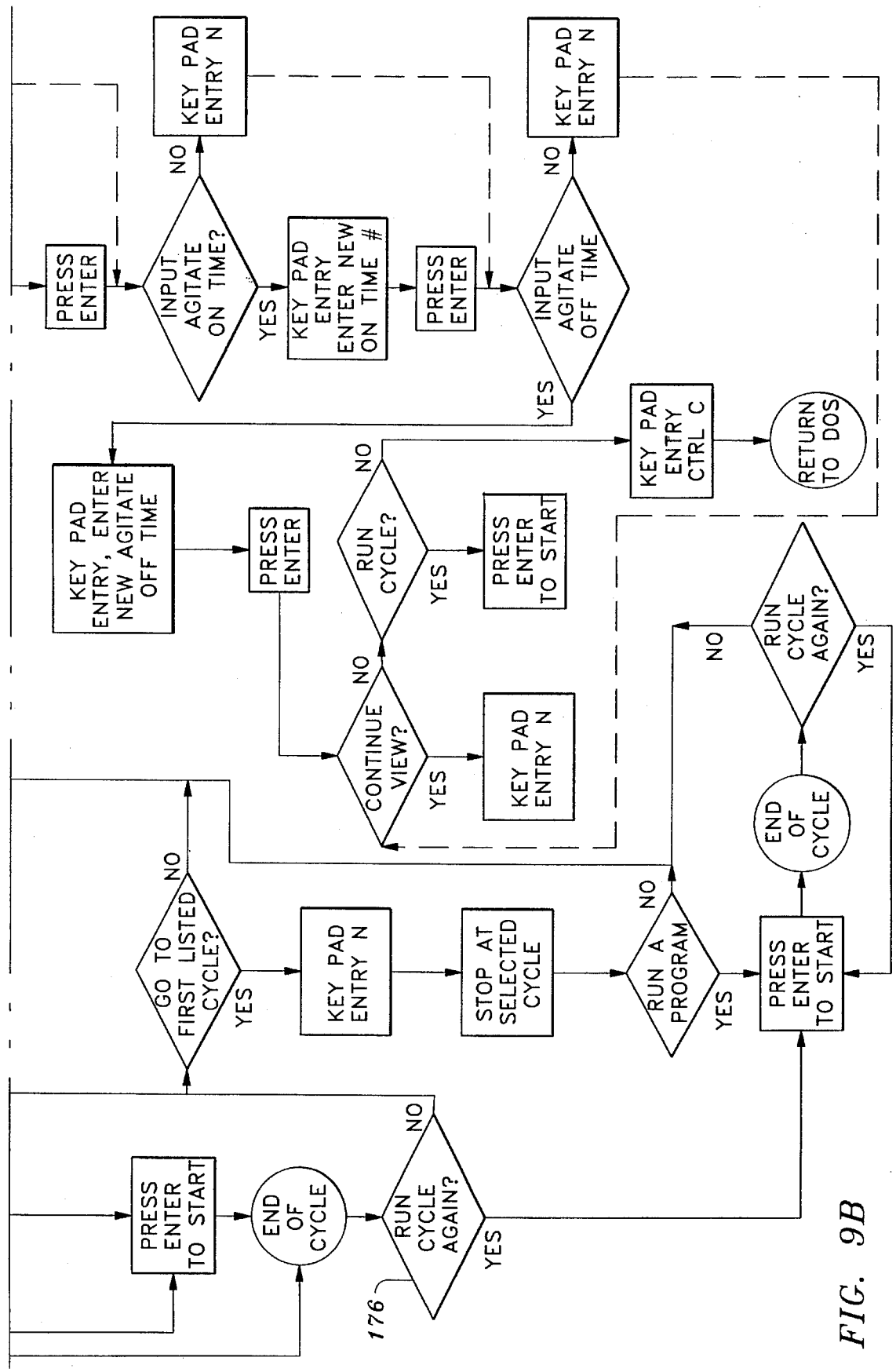

When the appropriate method has been selected (or written), the WordStar program is left by the command "Control Kx," operation block 165 followed the entry of the letter "M" (operation block 170) at the system prompt when operating with a DOS operating systems. Referring now to FIGS. 9A and 9B, the control program is shown schematically. It can be seen in FIGS. 9A and 9B that the operator can select any program by viewing all the cycles (decision box 172) and then run that cycle (decision box 174). The program then permits the user to run the cycle again (decision box 176), select a new cycle (box 172) or change the process (box 178).

Once methods are selected and the instrument is conducting a run, a standard computer monitor displays the instrument's current program progress. Upon completion, if an identical second run is desired, it can be initiated by a single command.

The apparatus of this invention meets stringent requirements for successful post-blotting processing. It is a fully programmable and automated instrument able to perform functions for single or multiple post-blot developments. It controls timing, temperature, agitation, and reagent volumes for any number of consecutive stored protocols.

The detailed description of the apparatus, its components and the method of use is provided in FIGS. 1–9B.

UTILITY

The utility of this invention encompasses a broad scope of assays involved in post developmental processes. These assays and processes can be pre-set in the apparatus and in the computer program or they can be defined by end users according to their specific research and diagnostic needs.

An apparatus of this invention is totally flexible, versatile, convertible and achieves maximum efficiency with regard to number of samples being processed using single method with common reagents. The apparatus is also fully convertible and can be easily used for several different sets of assays separately or combine these assays in any way desirable to a user.

This invention is useful for both research and clinical application in diagnostic as well as prognostic evaluation.

Specifically, for research and development, the apparatus and method are useful for identification of specific antigens, for assessment of the quality of specific protein, peptide or DNA, for identification of similar protein in multiple forms in IEF or Native PAGE, or for identification of specific component in 2-D SDS-PAGE. For detection, identification and quantitation of nucleic acid, nucleic acid containing structures specific receptor bindings, peptides, polypeptides, proteins, hormones, and antigen-antibody complexes.

As a clinical, diagnostic and prognostic tool, the apparatus of this invention is useful for identification of specific final product in processing, for monitoring specific product during processing or for selecting specific product in pooled samples during processing.

While the invention has general utility, it is preferably used for immunological and nucleic acid transfers to specifically isolate and identify proteins or DNA or DNA fragments.

The invention is illustrated in the following examples. These examples are offered by way of illustration and should not be interpreted in any way to be limiting the scope of the invention.

EXAMPLE 1

Semi-dry Electroblotting Post-transfer Assay

This example illustrates a post-transfer separation assay using a specific antibody used after the primary semi-dry electroblotting processing of the protein.

Three sheets of polyvinyldifluorourethane membrane were placed side by side into a reaction chamber. The sheets were separated by a polypropylene mesh in order to prevent intersheet connection. Each sheet contained 17 kilo-Dalton (kD) protein suspended within its matrix, obtained by a preceding process known as semi-dry electroblotting described by Kyhse-Andersen in *J. Biochem. Biophys. Methods*, 10:203–209 (1984) incorporated hereby by reference. The three sheets placed in the reaction chamber were soaked with a sufficient volume of electroblotting anode #1 buffer, comprising 0.3% Tris (hydroxymethyl) aminomethane and, 20% methanol at pH 10.4. The reaction chamber lid was securely fastened and the desired and established protocols of reagents to be used and their sequence were introduced by a start command from the digital computer.

The first step of the post-transfer assay

The first reagent to enter the reaction chamber was a blocking solution to inhibit remaining active sites on the membranes. The process of maintaining the membranes in the blocking solution was noted as the incubation period and was performed at room temperature. The blocking incubation process lasted 30 minutes. The blocking solution which was introduced contained 5% bovine serum albumin 5% serum; five percent non-fat dry milk or 1% ovalbumin was optionally used to supplement the solution content. After 30 minutes of the incubation period of the first reagent, the blocking solution was transferred from the reaction chamber into a reclamation system by using vacuum, as described in FIG. 7.

The second step of the post-transfer assay

The addition of a second reagent followed immediately. The second reagent was distilled water used to rinse away the blocking solution from the reaction chamber. This process was repeated three times for two minutes each.

The third step of the post-transfer assay

After the final rinse was removed from the reaction chamber, the addition of the first binding antibody was initiated. Upon entry of binding reagent into the reagent chamber, the contents of the reaction chamber were agitated by the air bladder. The binding antibody-containing reagent comprises the solution of purified anti-Rabbit anti-serum (10 micrograms per milliliter). In alternative or additionally, serum (1 to 1000 dilution); mouse monoclonal cell antibody containing ascites fluid (1 to 1000 dilution); mouse monoclonal culture supernatant (1 to 100 dilution) may also be used. The binding antibody solution was then removed from the reaction chamber into a reagent reclamation system, as described above.

The fourth step of the post-transfer assay

The next step included moving of the washing solution to the reaction chamber for another washing cycle with 500 ml of the wash solution, followed by ten minutes of agitation. The washing cycle was repeated three times under the same conditions. The wash solution comprised 0.1% Tween 20.

The fifth step of the post-transfer assay

Once the third wash solution exited the reaction chamber, a goat anti-rabbit antibody, conjugated to horse radish peroxidase, dissolved in 180 ml of binding buffer was moved into the reaction chamber and incubated for 2 hours at room temperature. The antibody solution was moved from the reaction chamber to the reagent reclamation system.

The sixth step of the post-transfer assay

A washing solution (500 ml) was again used to rinse the reaction chamber. The rinsing was done ten minutes with a washing solution comprising 0.1% Tween 20 in phosphate-buffered saline (20 mM potassium-sodium phosphate at pH 7.5 with 0.9% sodium chloride/weight/volume (w/v)). The washing cycle was repeated three times and lasted each time for ten minutes. After the final wash, the washing solution was moved from the reaction chamber to a reagent reclamation system.

The seventh step of the post-transfer assay

In the next step, the signal development and quantitation reagent, i.e., a substrate for horseradish peroxidase, was introduced into the reaction chamber for five minutes and was then transferred into a reagent reclamation system. The substrate solution contained 100 ml of PBS, pH 7.2. 0.3% hydrogen peroxide, and 50 mg 3,3'-diaminobenzidine. The substrate generated a color signal which is quantified on the basis of the amount of antigen present.

The final step of the post-transfer assay

After the removal of the substrate solution, a final rinse of distilled water was introduced into the reaction chamber three times for two minutes each time. During the final assay, bands appeared on the three membranes indicating specificity of the 17 kD protein. The intensity of the band was measured against a known standard value showing that 17 kD protein can be quantified.

EXAMPLE 2

Staining SDS-PAGE and the Blotted Membrane from Western Blot

This example illustrates a developmental procedure for a pre-transfer SDS-PAGE (sodium dodecyl sulfate polyacrylamide gel electrophoresis) and a post-transfer separation by using Coomassie Blue G250 stain.

Proteins of 26 kD and 13 kD were separated on a 15% acrylamide SDS-PAGE. This SDS-PAGE gel of 10×15 cm was placed in the reaction chamber of the apparatus. About 25 ml of fixing solution containing 5% acetic acid and 10% methanol was transferred into the chamber. The gel was agitated in the solution for 5 minutes at room temperature.

A nylon membrane of 10×15 cm was wet with distilled water, laid on the gel and electroblotted with a semi-dry electrotransfer apparatus for 10–15 minutes according to Kyhse-Andersen publication, cited in Example 1.

The SDS-polyacrylamide gel was then placed in the reaction chamber 28 of the present apparatus, and the nylon membrane was left in the fixing solution for further staining. After securing the lid, 25 ml of 0.1% Coomassie Blue G250 solution (0.1% Coomassie Blue G250 w/v/ in the fixing solution) was transferred into the chamber. The temperature was programmed to 40° C. and the chamber was agitated gently for 5–10 minutes.

The staining solution was then withdrawn and recycled into the reservoir pouch. 50 ml of the destaining solution (5% acetic acid, 15% ethanol) was transferred into the chamber and was agitated for 10 minutes. Then, the destaining solution was drained to the waste pouch. This step was repeated twice.

Then, 25 ml of 5% acetic acid was transferred into the chamber and after 10 minutes of agitation, the solution was drained and the successfully stained gel was taken out of the chamber for drying.

The nylon membrane was then placed in the reaction chamber and processed similarly to Example 1 with the following steps:

a) blocking with serum albumin solution;
b) rinsing several times with distilled water;
c) incubating with rabbit anti-13 kD protein antibody;
d) washing several times with 0.1% Tween 20 solution in PBS;
e) incubating with goat anti-rabbit antibody-HRP conjugate;
f) washing several times with Tween 20 solution;
g) incubating in the substrate solution using diaminobenzidine; and
h) rinsing with distilled water several times.

The result of the SDS-PAGE alone showed two bands stained with Coomassie Blue at 26 and 13 kD region. However, the membrane with both bands blotted, showed only the 13 kD band being lit up with the specific antibody, in accordance with the rinsing, incubating and washing steps of the present process.

EXAMPLE 3

Blotting DNA (Southern) or RNA (Northern) onto a a Nitrocellulose Membrane and Hybrizing with a Radioactive Oligonucleotide Probe This example illustrates Southern and Northern blotting DNA assays useful in the current invention.

This is a generalized example applicable to both DNA or RNA hybridization on a nitrocellulose membrane. The probe used had a specific activity of $10^8$ cpm/ug RNA. A limited volume of 5 ml of probe was used and was recycled and stored in one of the reservoir pouches. In order to avoid radioactive contamination, the lines and the reaction chamber were flushed with acid (10% phosphoric acid) and base (0.1N NaOH) and then with distilled water.

A nitrocellulose membrane, 10×15 cm, with the RNA bands blotted thereon was placed in the reaction chamber and 5 ml of the hybridization buffer A (6X SSC, 1% SDS, 0.1% Tween 20, 50% deionized formamide, 100 ug/ml tRNA) was transferred into the reaction chamber, after securing the chamber lid. The chamber was heated to 50° C. and agitated gently for 15 minutes.

The Buffer A was removed, and 5 ml of fresh Buffer A containing $10^6$ cpm/ml of the radioactive RNA probe was added and agitated gently at 50° C. for 12 hour (overnight).

The radioactive RNA solution was then collected in an empty designated reservoir pouch.

10 ml of the 1X SSC, 0.1% SDS (0.15M NaCl, 0.015M sodium citrate at pH 7) solution was delivered through the lines and into the chamber, at 22° C. with gentle agitation for 30 minutes. This was repeated twice.

10 ml of the 0.1X SSC, 0.1% SDS solution was then transferred into the chamber at 65° C. with gentle agitation for 30 minutes. This was repeated twice.

The membrane was taken out and exposed to X-ray film for 2 hours at 4° C. and the film was then developed. The film showed bands where the radiolabelled RNA probe had bound to the fixed DNA or RNA samples.

The aboveprocedure is described in detail in Melton, D., et al., *Nucleic Acids Res.*, 12: 7035–56 (1984); and Church, G. and Giklbert, W. *Proc. Natl. Acad. Sciu.*, (U.S.A.), 81: 1991–95 (1984), hereby incorporated by reference.

EXAMPLE 4

Immunofluorescent Labelling of Sectioned Tissue

This example illustrates the use of this invention for immunofluorescent labelling of sectioned tissue.

This is a generalized example of staining a biological tissue sample, either as a whole or sectioned in a cryotomised or wax-embedded configuration. In this case, the staining is immunologically enhanced using a streptavidin fluorochrome conjugate.

A cryosectioned brain tissue was dried on a microscopic slide and placed in the reaction chamber of the present apparatus.

10 ml of 75% ethanol was then added, agitated for 30 minutes and then removed. 10 ml of PBS as in Example 1 was added, agitated for 10 minutes, and removed. This was repeated twice. 5 ml of a rabbit anti-NGF receptor antibody (1:1000) in PBS, was added, agitated for 30 minutes at 37° C., and recycled into a designated empty reservoir pouch. The tissue was then washed with 10 ml 0.1% Tween 20 in PBS with agitation for 10 minutes. This was repeated twice. Blocking solution (10 ml 1% BSA in PBS, as in Example 1) was then added, incubated for 15 minutes at 37° C., and removed. This was repeated once. The tissue was then washed with 10 ml of 0.1% Tween 20 in PBS with agitation for 15 minutes. This was repeated twice.

Biotinylated goat anti-rabbit antibody (5 ml 1:1000) in PBS was added and incubated for 30 minutes at 37° C. with agitation. This was removed and collected in another designated empty pouch for recycling.

The tissue was then washed with 10 ml of 0.1% Tween 20 in PBS with agitation for 15 minutes. This was repeated twice.

Streptavidin-fluorochrome conjugate (10 ml, Vector Labs) and was added and incubated for 13 minutes at 37° C., and transferred into a third empty pouch for recycling. The tissue was then washed with 10 ml of PBS with agitation for 15 minutes. This was repeated four times.

At this point, the slide was removed and observed under a fluorescent microscope. Antibodies bound to NGF receptor in the tissue were observed.

The above-described procedure is further described in Coons, A. H., Creech, H. J., and Jose, R. N. *Proc. Soc. Exp. Biol. Med.*, 47:200–202, (1941) the disclosure of which is hereby incorporated by reference.

The foregoing description of the preferred embodiments of the present method and apparatus are to be construed as exemplary and not limiting. The scope of the present invention is defined by the following claims.

What is claimed is:

1. A device for treating reactant-carrying bodies with predetermined sequences of reagents, comprising:

a housing;

a reagent pouch container which is receivable in said housing and is manually removable therefrom without tools; at least one reagent pouch which is receivable in said reagent pouch container and is manually removable therefrom without tools, is capable of independently containing a quantity of a fluid reagent, and is provided with a valved conduit coupling capable of passing fluid only when coupled to another valved conduit coupling;

at least one flexible tubular conduit which is provided at each end with one of said valved conduit couplings;

a reactant-carrying body container which is receivable in said housing and is manually removable therefrom without tools;

at least one electrically operable pinch valve which is contained in said housing;

at least one transfer conduit for conducting fluid reagent from one of said reagent pouches to said reactant-carrying body container, which transfer conduit includes one of said flexible tubular conduits which passes through one of said pinch valves;

pressurized gas source means for supplying gas under superambient pressure to the interior of said reagent pouch container, whereby to compress all of the reagent pouches which are contained within said reagent pouch container; and programmable control means for controlling the operation of said pinch valves.

2. A device for treating reactant-carrying bodies with predetermined sequences of reagents as claimed in claim 1, further comprising agitating means for agitating said reactant-carrying body container at times and for intervals determined by said programmable control means.

3. A device for treating reactant-carrying bodies with predetermined sequences of reagents as claimed in claim 2, further comprising a reagent reclamation system including a plurality of waste reagent receptacles, a plurality of reagent conduits, each extending from said reactant-carrying body container to one of said waste reagent receptacles and passing through an electrically operable waste flow control valve, and vacuum source means for providing vacuum for drawing waste reagent from said reactant-carrying body container into selected ones of said waste reagent receptacles under the control of said programmable control means.

4. A device for treating reactant-carrying bodies with predetermined sequences of reagents as claimed in claim 2, in which said housing is provided with a lid having apertures through which said reagent pouch container and said reactant-carrying body container project.

5. A device for treating reactant-carrying bodies with predetermined sequences of reagents as claimed in claim 4, in which said programmable control means is received in said housing, and in which said lid of said housing is provided with an aperture through which said programmable control means can be operated.

6. A device for treating reactant-carrying bodies with predetermined sequences of reagents as claimed in claim 1, further comprising a reagent reclamation system including a plurality of waste reagent receptacles, a plurality of reagent conduits, each extending from said reactant-carrying body container to one of said waste reagent receptacles and passing through an electrically operable waste flow control valve, and vacuum source means for providing vacuum for drawing waste reagent from said reactant-carrying body container into selected ones of said waste reagent receptacles under the control of said programmable control means.

7. A device for treating reactant-carrying bodies with predetermined sequences of reagents as claimed in claim 1, in which said housing is provided with a lid having apertures through which said reagent pouch container and said reactant-carrying body container project.

8. A device for treating reactant-carrying bodies with predetermined sequences of reagents as claimed in claim 7, in which said programmable control means is received in said housing, and in which said lid of said housing is provided with an aperture through which said programmable control means can be operated.

9. A device for treating reactant-carrying bodies with predetermined sequences of reagents as claimed in claim 1, in which said reagent pouch container contains a plurality of reagent pouch supporting means for supporting individual ones of said reagent pouches and has a corresponding plurality of conduits passing through one of its walls, and in which each of said conduits is provided with one of said valved conduit couplings at each of its ends.

* * * * *